Aug. 6, 1957 E. S. BOERNER Plant Pat. 1,628
ROSE PLANT
Filed Nov. 29, 1956
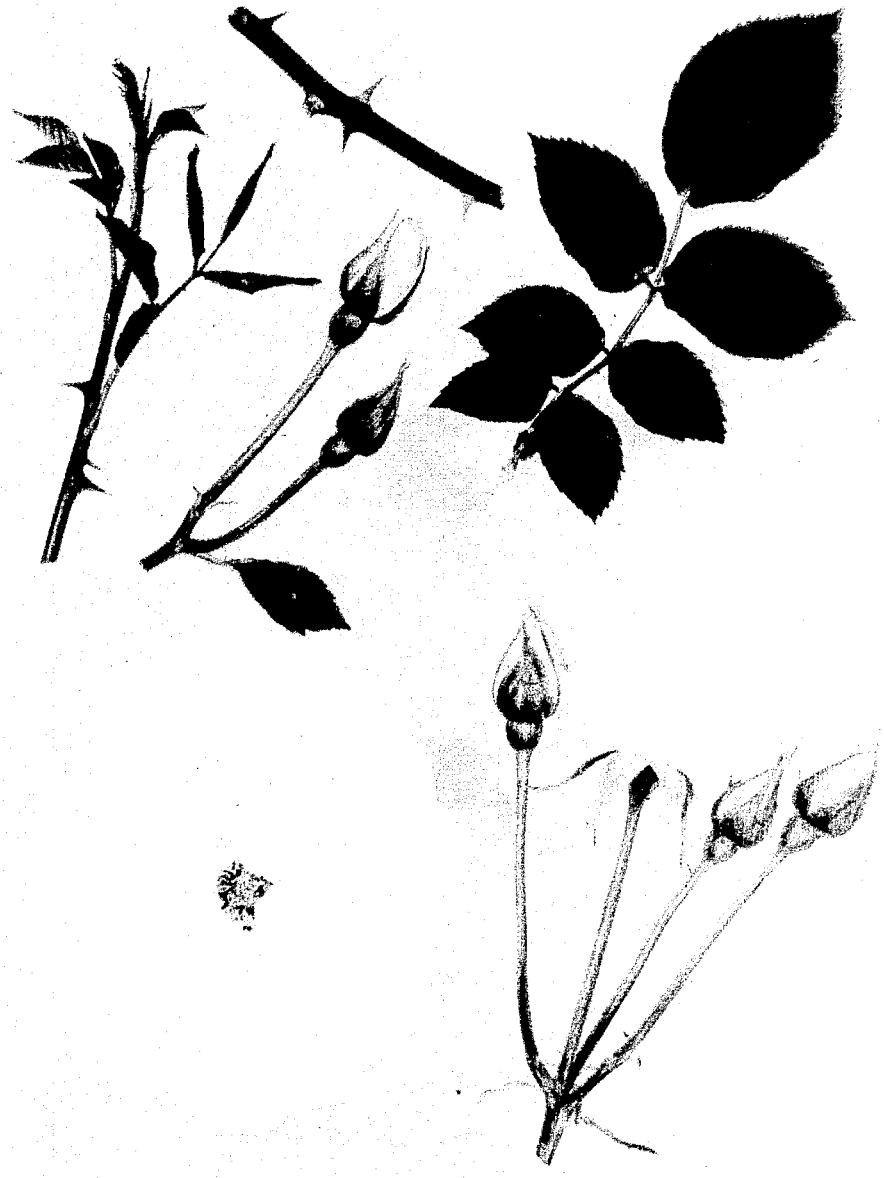
Inventor.
E. S. Boerner
By: Robb & Robb
Attorneys.

United States Patent Office

Plant Pat. 1,628

Patented Aug. 6, 1957

1,628

ROSE PLANT

Eugene S. Boerner, Newark, N. Y., assignor to Jackson & Perkins Company, Newark, N. Y., a corporation of New York Application November 29, 1956, Serial No. 625,202

1 Claim. (Cl. 47—61)

The present invention relates to a new and distinct variety of rose plant of the large-flowered polyantha class, which was originated by me by crossing an unnamed and unpatented white hybrid tea seedling of "Starlite" (unpatented) with an unnamed and unpatented white floribunda seedling of "Glacier" (Plant Patent No. 1,025).

The primary objective of this breeding was to produce a new rose variety of the floribunda class which bears longer-lasting flowers that are better suited for cut flower purposes than other varieties of this class. This objective was fully achieved, along with other improved features, as evidenced by the following characteristics which are outstanding in the new variety and distinguish it from its parents and from all other varieties of which I am aware:

(1) The leathery and crisp texture of the flower petals:

(2) The slow-opening habit of the blooms; and (3) The long-lasting quality of the flowers which frequently will keep fresh for as long as ten days under normal room conditions.

Asexual reproduction of my new variety, by budding, as performed at Newark, New York, and also at Pleasanton, California, shows that the aforementioned characteristics come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed white hybrid tea seedling of "Starlite."

*Pollen parent.*—An unnamed white floribunda seedling of "Glacier."

Classification:

*Botanic.*—Large-flowered polyantha.

*Commercial.*—Floribunda.

*Flower*

(Observations made from speciments grown in a greenhouse at Newark, New York, in the early afternoon and in the latter part of May.)

Blooming habit: Recurrent—continuous.

Bud:

*Size.*—Medium.

*Form.*—Pointed; ovoid; is not affected by wet or hot weather.

*Color.*—When sepals first divide.—Pale Chalcedony Yellow, Plate 17. When petals begin to unfurl—Sea-Foam Green, Plate 31. When half-blown: Inside of petals—White, Plate 53, lightly overcast with Marguerite Yellow, Plate 30. Reverse of petals—White, Plate 53, lightly overcast with Sea-Foam Yellow, Plate 31.

*Sepals.*—Branched; curl back when petals begin to unfurl. Color: inside—Turtle Green, Plate, 32. outside—Light Bice Green, Plate 17.

*Calyx.* — Color — Light Bice Green, Plate 17. Shape — pear. Size — small. Aspect — smooth. Odor when rubbed—none.

*Peduncle.*—Length — medium. Aspect — smooth. Strength—erect; slender. Color—Biscay Green, Plate 17.

*Opening.*—Opens up well; is not affected by adverse weather conditions.

Bloom:

*Size.*—Medium. Average size when fully expanded—four inches.

*Borne.*—In irregular clusters.

*Stems.*—Medium length; normal strength.

*Form (when first open).*—Cupped. Permanence—flattens; outer petals curl back and all petals curl at tip.

*Petalage.*—Double (full but open center). Number of petals under normal conditions—from 30 to 35.

*Color.*—Center of flower—White, Plate 53, with lower half of petal lightly overcast with Marguerite Yellow, Plate 30. Outer petals—White, Plate 53. Base of petals (aiglet)—Sea-Foam Yellow, Plate 31. Inside of petals—White, Plate 53. Reverse of petals—White, Plate 53. General tonality from a distance—White, Plate 53.

*Discoloration.*—General tonality at end of first day—White, Plate 53. Second day—White, Plate 53. Third day—White, Plate 53.

Petals:

*Texture.*—Leathery; crisp; is not affected by wet or hot weather.

*Appearance.*—Inside—satiny. Outside—shiny.

*Form.*—Oval; slightly notched.

*Arrangement.*—Irregular.

*Petaloids in center.*—Few; small.

*Persistance.*—Drop off cleanly.

*Fragrance.*—Moderate. Nature—vanilla.

*Lasting quality.*—On the plant—very long. As cut flower—very long; frequently as long as ten days under normal room conditions.

*Genital organs*

Stamens, anthers: Small; many; regularly arranged around styles. Color—Mikado Brown, Plate 29.

Stamens, filaments (threads): Medium length. Color—Sea-Foam Yellow, Plate 31.

Pollen: Color—Light Vinaceous-Cinnamon, Plate 29.

Styles: Bunched; uneven length; short; thin.

Stigmas: Color—Pale Ochraceous Salmon, Plate 15.

Ovaries: All enclosed in calyx.

Hips: None.

Seeds: None.

*Plant*

Form: Bush.

Growth: Vigorous; branching.

Foliage: Compound of 5 to 7 leaflets.

*Size.*—Large.

*Quality.*—Normal.

*Color.*—New foliage: upper side—Lettuce Green, Plate 5, with outer edge of leaf and serrations, Garnet Brown, Plate 1; under side—Yellowish Oil Green, Plate 5, lightly overcast with Bordeaux, Plate 12. Old foliage: upper side—Yew Green, Plate 31; under side—Light Elm Green, Plate 17.

*Shape.*—Oval pointed.

*Texture.*—Upper side—leathery. Under side—smooth.

*Ribs and veins.*—Ordinary.

*Edge.*—Serrated (sawtoothed).

*Serrations.*—Both double and single; small.

*Leaf stem.*—Color—Cress Green, Plate 31. Under side—smooth.

*Stipules.*—Medium length; smooth.

Wood:

*New Wood.*—Color—Hellebore Green, Plate 17. Bark—smooth.

*Old wood.*—Color—Dark Cress Green, Plate 31. Bark—smooth.

Thorns:

*Thorns.*—Quantity: on main stalks from base—Ordinary; on laterals from stalk—ordinary. Form—broad base; long; straight; very stiff and strong.

Color (when young)—Old Rose, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the leathery and crisp texture of its flower petals, by the slow-opening habit of its blooms, and by the long-lasting quality of its flowers as cut flowers.

No references cited.